(12) United States Patent
Tadimety et al.

(10) Patent No.: US 11,808,763 B2
(45) Date of Patent: Nov. 7, 2023

(54) METHOD AND APPARATUS FOR ORDERED NANOPLASMONIC SENSOR FORMATION THROUGH MICROFLUIDIC ASSEMBLY

(71) Applicant: THE TRUSTEES OF DARTMOUTH COLLEGE, Hanover, NH (US)

(72) Inventors: Amogha Tadimety, West Lebanon, NH (US); John X. J. Zhang, Hanover, NH (US)

(73) Assignee: THE TRUSTEES OF DARTMOUTH COLLEGE, Hanover, NH (US)

(*) Notice: Subject to any disclaimer, the term of this patent is extended or adjusted under 35 U.S.C. 154(b) by 882 days.

(21) Appl. No.: 16/492,128

(22) PCT Filed: Mar. 7, 2018

(86) PCT No.: PCT/US2018/021392
§ 371 (c)(1),
(2) Date: Sep. 7, 2019

(87) PCT Pub. No.: WO2018/165331
PCT Pub. Date: Sep. 13, 2018

(65) Prior Publication Data
US 2021/0132054 A1    May 6, 2021

Related U.S. Application Data

(60) Provisional application No. 62/468,499, filed on Mar. 8, 2017.

(51) Int. Cl.
*G01N 33/543* (2006.01)
*G01N 21/552* (2014.01)
(Continued)

(52) U.S. Cl.
CPC ..... *G01N 33/54373* (2013.01); *G01N 21/554* (2013.01); *G01N 33/54346* (2013.01);
(Continued)

(58) Field of Classification Search
CPC ........... G01N 33/54373; G01N 21/554; G01N 33/54346; G01N 33/553; G01N 21/552; B82Y 15/00; B82Y 30/00
(Continued)

(56) References Cited

U.S. PATENT DOCUMENTS 8,883,094 B2    11/2014    Huo et al.
2012/0184451 A1    7/2012    Singamaneni et al.
2016/0252512 A1    9/2016    Han et al.

FOREIGN PATENT DOCUMENTS

WO    WO 2016/133899 A1    8/2016

OTHER PUBLICATIONS

International Patent Application No. PCT/US2018/021392; International Search Report and Written Opinion dated May 14, 2018; 10 pgs.
(Continued)

*Primary Examiner* — Christopher L Chin
(74) *Attorney, Agent, or Firm* — Cozen O'Connor

(57) ABSTRACT

A method of making a plasmon-resonance biosensor includes conjugating precious metal nanorods with form factor at least 1.5 with a biological probe material. Microfluidic chambers of volume under 0.025 microliter are formed over a substrate, and an aqueous suspension of the conjugated nanorods is injected into the chambers. The nanorods are organized in rows and aligned in long dimension along the rows. The biosensor is configured to be read by obtaining an optical absorption spectrum upon exposure to the analyte. The biosensor includes precious metal nanorods organized in rows with long dimension approximately parallel to the rows. The nanorods are conjugated with biological probes capable of binding to an analyte, the
(Continued)

probes may be an aptamer, an antibody, a protein-nucleic acid (PNA), a complimentary DNA, or an enzyme having a binding site.

19 Claims, 8 Drawing Sheets

(51) Int. Cl.
  *G01N 33/553* (2006.01)
  *B82Y 15/00* (2011.01)
  *B82Y 30/00* (2011.01)
(52) U.S. Cl.
  CPC ............ *G01N 33/553* (2013.01); *B82Y 15/00* (2013.01); *B82Y 30/00* (2013.01)
(58) Field of Classification Search
  USPC .............. 435/7.92, 7.21; 436/523, 533, 525; 977/918, 920; 356/301, 136, 133, 432; 427/122, 220; 428/119, 148
  See application file for complete search history.

(56) References Cited

OTHER PUBLICATIONS

Tebbe et al. (2015), "Optically anisotropic substrates via wrinkle-assisted convective assembly of gold nanorods on macroscopic areas," Faraday discussions, vol. 181, pp. 243-260.

Rey et al. (2013), "Deterministic assembly of linear gold nanorod chains as a platform for nanoscale applications," Nanoscale, vol. 5, No. 18, pp. 8680-8688.

Nguyen et al. (2015), "Nanoplasmonic biosensor: Detection and amplification of dual bio-signatures of circulating tumor DNA." Biosensors and Bioelectronics, vol. 67, pp. 443-449.

Chen et al. (2015), "Combined detection of breast cancer biomarkers based on plasmonic sensor of gold nanorods," Sensors and Actuators B: Chemical, vol. 221, pp. 1391-1397.

Nam et al. (2016) "Nanofluidic flow assisted assembly of dispersed plasmonic nanostructures into shallow nanochannel sensors." Journal of Vacuum Science & Technology B, Nanotechnology and Microelectronics: Materials, Processing, Measurement, and Phenomena. vol. 34 No. 6, pp. 1-8.

Hanske et al. (2014), "Strongly Coupled Plasmonic Modes on Macroscopic Areas via Template-Assisted Colloidal Self-Assembly," Nano Lett., 14, 12, 6863-6871.

Joshi et al. (2015), "Label-Free Nanoplasmonic-Based Short Noncoding RNA Sensing at Attomolar Concentrations Allows for Quantitative and Highly Specific Assay of MicroRNA-10b in Biological Fluids and Circulating Exosomes," ACS Nano. Nov. 24, 2015;9(11):11075-89. doi: 10.1021/acsnano.5b04527.

Nguyen et al. (2015) "Nanoplasmonic biosensor: Detection and amplification of dual bio-signatures of circulating tumor DNA," Biosensors and Bioelectronics, vol. 67, 7 pp.

PCT/US2018/021392 International Preliminary Report on Patentability dated Sep. 10, 2019, 8 pp.

PCT/US2018/021392 International Search Report and Written Opinion dated May 14, 2018, 10 pp.

Rey et al. (2013) "Deterministic assembly of linear gold nanorod chains as a platform for nanoscale applications," Nanoscale, vol. 5, No. 18, 9 pp.

Tebbe et al. (2015) "Optically anisotropic substrates via wrinkle-assisted convective assembly of gold nanorods on macroscopic areas," Faraday Discussions, vol. 181, 243, 18 pp.

METHOD AND APPARATUS FOR ORDERED NANOPLASMONIC SENSOR FORMATION THROUGH MICROFLUIDIC ASSEMBLY

CLAIM TO PRIORITY

The present application is a 35 U.S.C. § 371 filing of International Application No. PCT/US2018/021392, filed Mar. 7, 2018, which claims priority to U.S. Provisional Patent Application No. 62/468,499 filed Mar. 8, 2017, the entire contents of which are incorporated herein by reference.

FIELD OF THE INVENTION

A fabrication method and apparatus for a low-cost, ordered nanoplasmonic sensor for biomarker detection.

SUMMARY

A method of making a plasmon-resonance biosensor includes conjugating precious metal nanorods with form factor at least 1.5 with a biological probe material. Microfluidic chambers of volume under 0.025 microliter are formed over a substrate, and an aqueous suspension of the conjugated nanorods is injected into the chambers. The nanorods are organized in rows and aligned in long dimension along the rows. The biosensor is configured to be read by obtaining an optical absorption spectrum upon exposure to the analyte.

A plasmon-resonance biosensor includes a plurality of precious metal nanorods, nanorods having form factor of at least 1.5, a maximum dimension under one half micron, are organized in rows with long dimension of the nanorods approximately parallel to the rows. The nanorods are conjugated with biological probes capable of binding to an analyte; the probes may be an aptamer, an antibody, a protein-nucleic acid (PNA), a complimentary DNA, or an enzyme having a binding site.

DETAILED DESCRIPTION OF THE EMBODIMENTS

Figure 1:
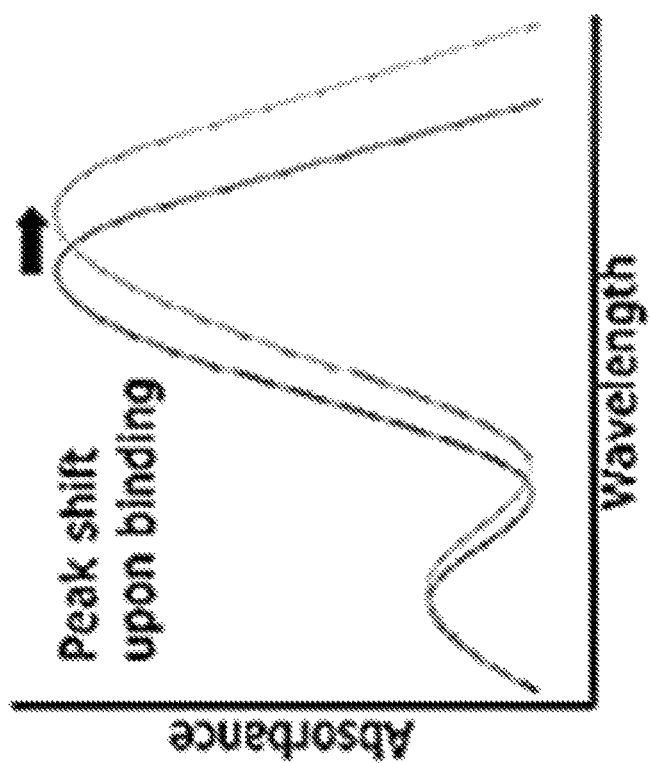
FIG. 1. Device Principle of Operation. The overall schematic of the device and operation. Functionalized nanoparticles are aligned on the substrate with capture probes and encased in a microfluidic device. Light is shined through the device and the absorbance is measured. Biomarker binding to the plasmonic particles causes a shift in the absorbance peak.
Figure 1:
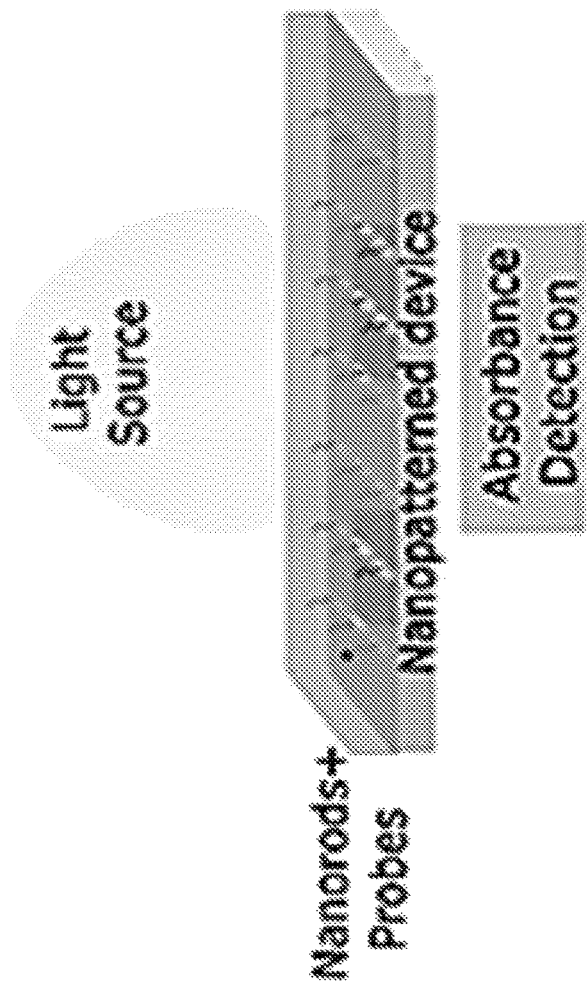

The concept of liquid biopsy and the promise of less invasive diagnostics are key to the emerging era of precision medicine, where early detection of disease can be accomplished through real time detection of clinically relevant biomarkers in low-volume human fluid samples such as blood. Plasmonic sensors, when combined with microfluidic chips, hold great promise because they offer a complete microsystem to perform both sample enrichment and detection. This combination allows sensitive, multiplexed and label-free detection of circulating tumor biomarkers at low concentration. Here we demonstrate an unconventional method to fabricate ordered nanorod arrays, where a nanowrinkle template was created first as an assembly site for nanorods deposition, screening of biomarkers, and plasmonic detection.

Tunable macroscale templates of nanowrinkles were formed using a simple stretch-release and plasma treatment process. Gold nanorods were then aligned over these nanowrinkle templates using custom microfluidic channels, enabling the near-field interactions of samples with the substrate and allowing the formation of micro-scale sensing spots. In order to produce consistent wrinkled templates, a custom polydimethylsiloxane (PDMS) stretcher was 3D printed to allow for slow release of the stretched and plasma-treated polymer. The templates were analyzed using atomic force microscopy (AFM) demonstrating wrinkles ranging from 30 to 100 nm in amplitude, and 50 nm to 1 micron in periodicity. Gold nanorods were then deposited into the templates using microfluidic channels with a grid of sensing spots for multiplexed sensing. Preliminary alignment results, taken using scanning electron microscopy (SEM), suggest that 80% of nanorods are aligned within 1 degree of rotation from the nanowrinkle axis, with 95% of the nanorods aligned within 5 degrees. Surface conjugation chemistry of the nanorods was designed to enhance electrostatic and wetting interactions for microfluidic-aided nanorod alignment within the wrinkles.

The optical extinction spectra of the nanoarrays were characterized using both computer modeling and a benchtop optical detection system. For wavelengths from 400 nm to 900 nm, nanoarray geometries were evaluated in terms of the sensitivity to refractive index variations and extinction spectrum, and the experimental results were compared to simulations. The benchtop optical detection system produced an extinction spectrum similar to the simulations, with an absorption peak from 500-900 nm and in a particular embodiment near 600 nm.

The demonstrated method of topologically wrinkled substrate fabrication combined with microfluidic chips can provide ordered nanoarrays with the dual function of biomarker enrichment and on-chip detection. This compact system requires a smaller concentration of noble metal particles with greater sample control.

The invention includes both a fabrication method and apparatus for a low cost, ordered nanoplasmonic sensor for biomarker detection.

We use localized surface plasmon resonance (LSPR) of this uniformly aligned gold nanorod material for detection of biomarker binding. LSPR detects binding on the surface of plasmonic particles due to changes in the localized dielectric environment. Aligned plasmonic particle deposition onto a glass slide improves upon existing devices due to LSPR sensitivity, ability to multiplex, and microfluidic integration. The rapid fabrication process also allows for lower fabrication costs. We believe that this invention is new because it improves fabrication costs as well as device performance compared to earlier technologies.

New and Unusual Features:

The two major classes of improvements include the fabrication process as well as the usability of the device. The two major sets of existing technology include surface-based microchips and solution-based sensors. Surface chips are more sensitive that sensors in solution, but are also very slow and expensive to produce. Our invention fills and improves the middle ground between these two classes because it is much easier and cheaper to fabricate than surface microchips while being more sensitive and usable than solution-based sensors. We believe this novelty makes it extremely marketable as an alternate low cost but more sensitive and versatile sensor chip.

Fabrication Advantages:

Low-cost—Typically, fabrication of ordered plasmonic nanostructures is costly because fabrication is often done using photolithography with electron beams or focused ion beams. This means that fabrication requires access to expensive high resolution microscopes. This invention's method of microfluidic alignment into surface topologies of templates is much lower cost with close to the same ordering capabilities. The cost of the polymer template is negligibly low, and the microfluidic alignment in particular keeps the fabrication low-cost by using minimal volumes of plasmonic particles (<0.05 ml of plasmonic nanoparticles per chip). This means that production using our method requires many fewer resources than traditional surface-based plasmonic sensors.

Rapid—Methods of substrate based chip fabrication are slow due to the beam drawing process. To get the resolution and area cover that we are able to achieve through the invention would require many microscope hours. Furthermore, these methods require expensive thermal evaporators to deposit noble metals onto the substrate surface. Our method of templating and stamping allows rapid fabrication of plasmonic chips from functionalized nanoparticles in under an hour. It requires nothing more than a wrinkled template, a microfluidic channel, and a solution of plasmonic particles. This template method is especially useful for larger-scale manufacturing because of its rapidity.

Usability and Sensitivity:

Sensitivity enhancement—Surface based microchips are superior in sensitivity to their solution-based counterparts because they are a monolayer of plasmonic particles. This monolayer behavior allows for clear focusing and minimal scattering compared to particles in solution. It also means that there is no worry of particle settling or coagulation which would detract from the sensitivity. Our invention has all of these sensitivity advances over solution-based assays. It also has the added advantage of aligned assembly, which further improves the sensitivity by reducing destructive scattering.

Versatility—The wrinkled templating method and microfluidic alignment are versatile for a range of plasmonic particles and sensing areas. Any nano- or micro-sized particle can be aligned using a wrinkled template and microfluidic flow: the same principles apply. This means that the method could be used for ordering of almost any plasmonic particle into a desired spacing over a desired area. It also means that the spacing and shapes of the nanoparticles can be very finely controlled depending on the application.

Readout—Because of the microfluidic assembly, the readout is significantly improved compared to existing devices. The shape, size, and locations of sensing spots can be finely controlled, meaning that this process can be tailored based on the method of readout apparatus. This is especially important in a field where wireless readout methods are increasing in popularity because it means that this methodology can be just slightly tweaked to keep up with improvements in readout capabilities.

One of the limitations is that as of now, the wrinkle-based templating can only align nanorods into ordered rows, not more complex circular shapes or bowtie antenna shapes. It may be possible to combine nanowrinkle templating with other techniques to produce other ordered shapes The proposed invention has commercial potential because of its low cost and sensitivity performance improvements. As described, the sensor can be used for capture of any biomarker. Because blood-based biomarkers have implications in cancer, prenatal testing, and infectious disease, this sensor fabrication method could be employed for detection in many diseases.

In terms of fabrication, the methodology used here improves upon existing plasmonic chip fabrication because of the templating method, and uses smaller amounts of noble metals due to microfluidic integration. Current methods of uniform nanorod deposition or fabrication are slow and expensive. Either an electron beam or focused ion beam is used, meaning that the process is painstaking and requires access to expensive equipment. The other option, incubation of substrate with plasmonic particle solution, is often an overnight procedure, but the described method takes only one hour to deposit particles, making it much more scalable than existing procedures. The proposed fabrication method also cuts down on the costs of traditional manufacture. Because of the microfluidic flow alignment, smaller volumes of nanoparticles and patient sample can be used and virtually no solution is lost. This significantly increases the efficiency of the manufacturing process, making it easy to produce many of these chips cheaply and rapidly.

In terms of performance, we believe that this technology will improve upon the sensitivity of similar devices. The aligned particles provide enhanced sensitivity because they minimize scattering. Because the chip is surface based and integrated with microfluidics, it has a number of advantages compared to solution-based sensors. The chip surface allows for higher sensitivity due to light focusing, increased enrichment of analyte due to microfluidics, and more controllable readout of the device.

The enhanced performance, versatility, and low-cost fabrication allow sensor manufacture to be scalable and multiplexed. This is highly relevant for companies who are working on blood-based diagnostics because of the wealth of information each sensor can provide.

Process Fabrication & Schematic

The nanobiosensor is commercializable because it uses recent advances in nanotechnology to optimize a low cost enhanced sensor for patient screening and monitoring.

FIG. 1 shows the sensor works through a change in light absorbance spectrum upon biomarker binding. The microchip is made through alignment of nanoparticles on a template and then stamped onto the glass substrate. Then a microfluidic device is incorporated to deliver the sample to the nanoparticles for binding and sensing. The microchip-based device has a baseline absorbance spectrum (shown in red), but if biomarkers are present in the sample the absorbance shifts towards the right (shown in blue). This is a very sensitive phenomenon, and allows detection of low concentration biomarkers. The sensitivity is improved by the alignment of particles achieved through the fabrication method.

Figure 2:
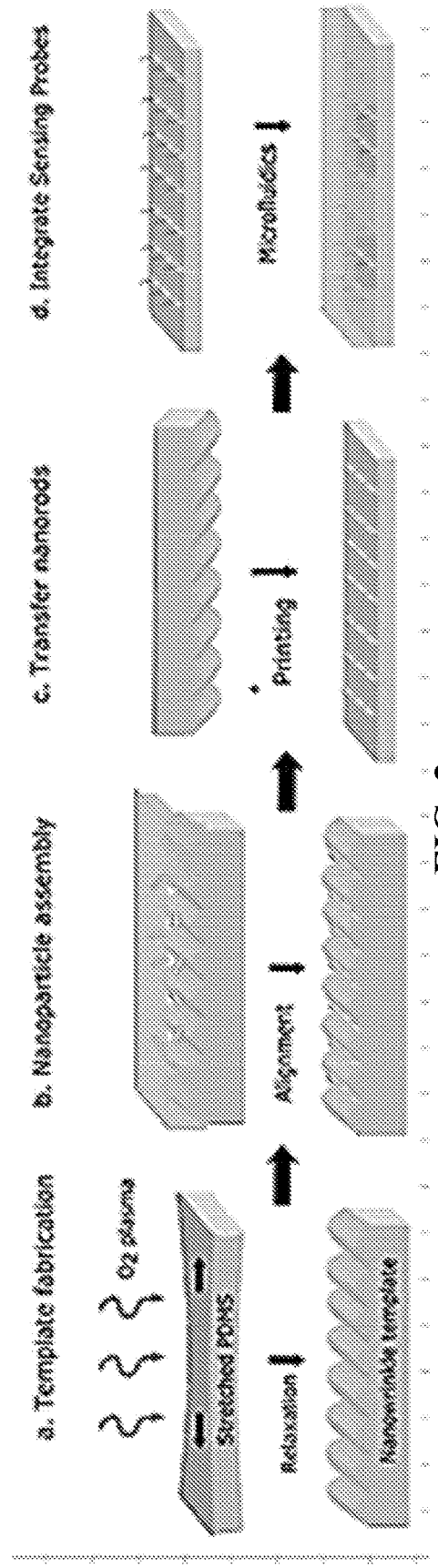
FIG. 2. Fabrication Schematic. The overall schematic of the device fabrication. PDMS template is stretched and reacted with $O_2$ plasma, creating nanowrinkles. Then, a microfluidic device is used to align nanoparticles, and the nanoparticles are stamped onto a glass substrate. Finally, a microfluidic device is used to integrate probes for capture.

FIG. 2 shows the schematic for fabrication of aligned nanoparticle based chip. First the polymer (PDMS) substrate is stretched and oxidized, and forms wrinkles upon relaxation. Then nanoparticles are assembled using controlled microfluidic flow, before they are stamped onto a glass substrate. Then a microfluidic channel is integrated for sample delivery.

Figure 3:
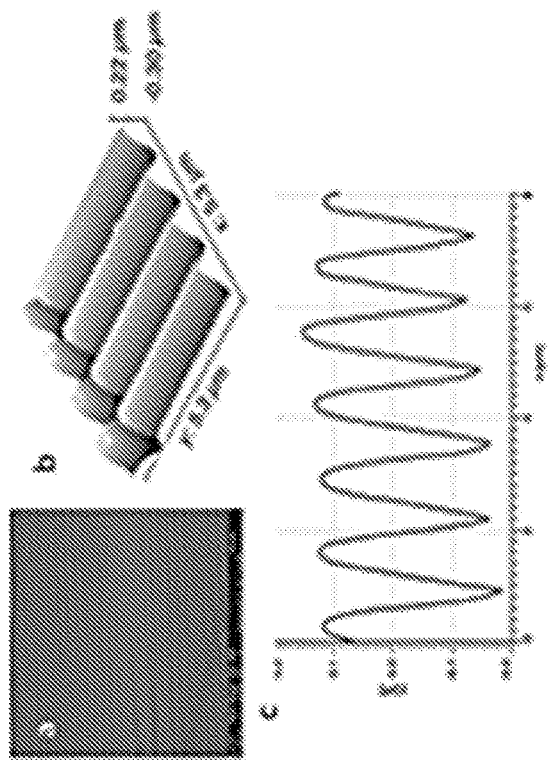
FIG. 3. Nanowrinkle Fabrication. The figure at the left shows the custom PDMS stretcher used to hold the polymer stretched for reaction. Inset (a) shows an SEM image of nanowrinkles, inset (b) shows an AFM scan of the wrinkle surface, and inset (c) shows a line profile of the wrinkles.
Figure 3:
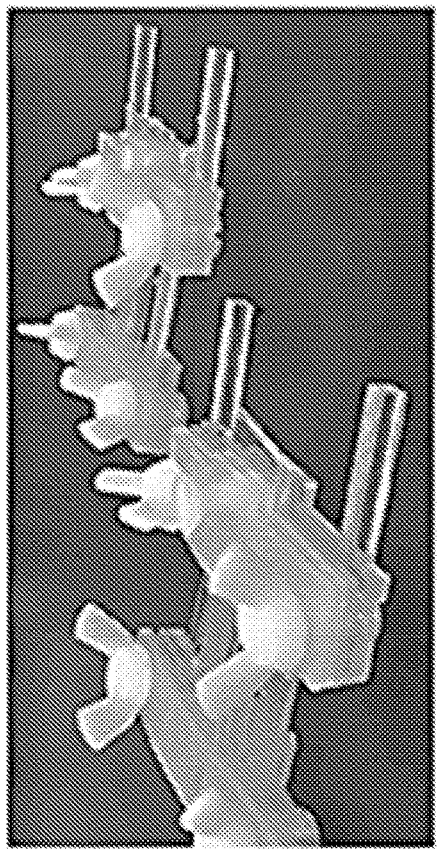

FIG. 3 shows some of the results from nanowrinkle fabrication, including the 3D printed PDMS stretcher, and SEM and AFM images of the wrinkled substrate. This process is tunable based on fabrication conditions for versatility of plasmonic particle choice.

Figure 4:
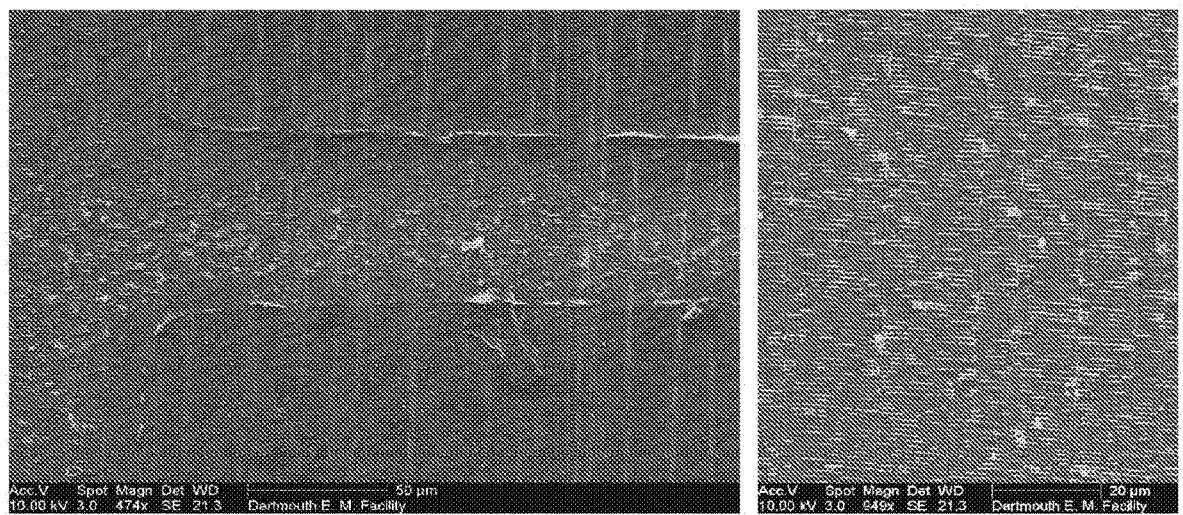
FIG. 4. Nanorod Alignment. On the left is a zoomed out version showing the microfluidic channel used for nanorod alignment, and on the right is a zoomed in photo showing nanorods aligned into the nanowrinkles. These can be used for sensing of biomarker binding.

FIG. 4 shows some of the results from microfluidic alignment of nanorods within wrinkles. In the figure on the left you can see a whole channel, and the right shows an inset of nanorods aligned within wrinkles.

Conjugating the Gold Nanorods.

The gold nanorods have surface plasmon resonances that change in optical absorption wavelength with a presence of bound polymer molecules such as protein or bound nucleic acid, and further change in wavelength when bound protein or nucleic acid in turn becomes bound to an analyte.

There are four types of biopolymer that may serve as biological probes to selectively bind analytes. These include proteins such as antibodies that are known to bind to specific antigens most commonly other proteins, and enzymes having peptide sequences at active sites that bind to specific molecules including enzyme substrates, enzyme inhibitors, and substrate analogs. These also include aptamers, aptamers including deoxyribose nucleic acid (DNA) or ribose nucleic acid (RNA) chains having ability to bind other molecules. They include DNA chains having sequences complementary to an analyte DNA or RNA chain and represented herein as cDNA. They also include protein nucleic acids (PNA) molecules having a polypeptide backbone with attached nucleic acids in a sequence complimentary to a targeted analyte DNA or RNA chain. The term biological probe as used herein includes antibodies, aptamers, cDNA, PNA molecules, and enzymes having a binding site for an analyte.

The gold nanorods may be conjugated with one or more biological probes.

It is known that many tumors spill nucleic acid chains due to apoptosis and other cellular functions, these nucleic acid chains may be specific to a tumor type, and may be found in circulating serum at concentrations far exceeding concentrations of the same or similar nucleic acid chains found in normal serum.

Figure 6:
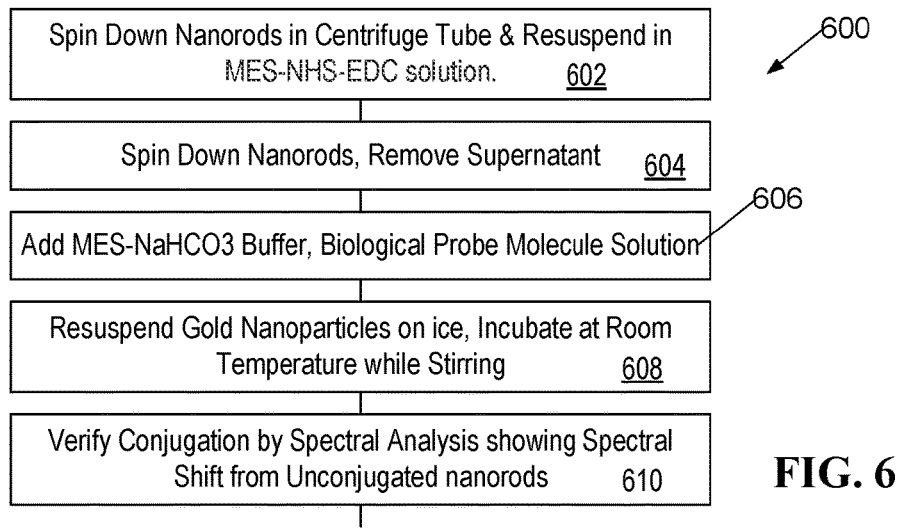
FIG. 6 is a flowchart of a method of conjugating nanorods to sensitized biopolymer.
Figure 5:
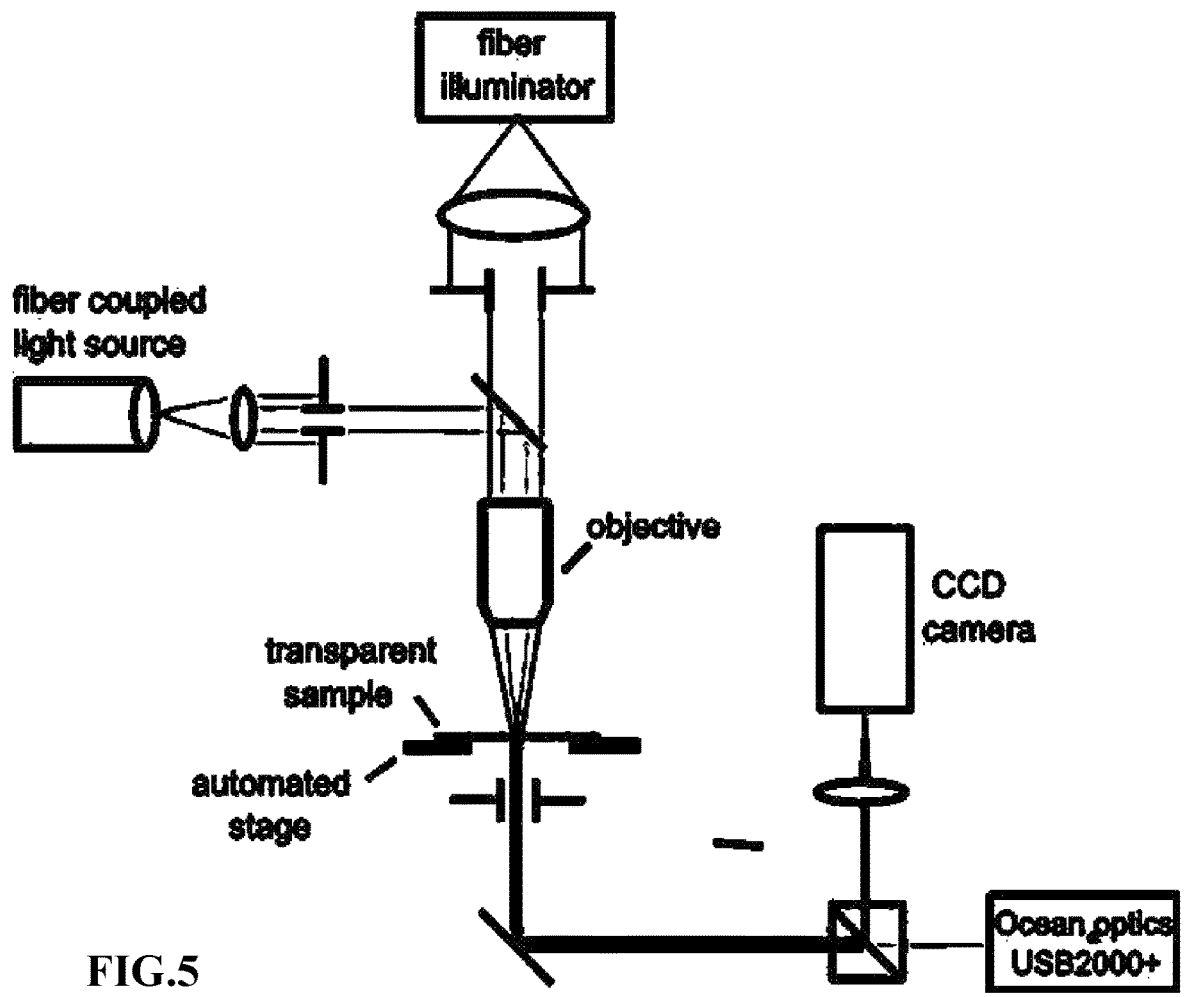
FIG. 5 is an illustration of an optical system adapted to reading the gold nanorod sensors herein described.

In an embodiment, the gold nanorods are conjugated 600 (FIG. 6) to a biological probe configured to bind to a deoxyribose nucleic acid (DNA) chain associated with specific tumor types. A PNA is synthesized having a nucleic acid sequence complementary to a desired analyte DNA chain is synthesized. This PNA strand-labeled carrier peptide is bound to gold nanorods as outlined in FIG. 6.

A portion of a stock suspension of gold nanorods is spun down in a centrifuge tube. A mixture of 98% 0.1 mill molar (mm) (N-morpholino)ethanesulfonic acid—0.5 mM sodium chloride (MES buffer) pH6, 1%—N-hydroxysuccinimide 937.5 mM (NHS stock), and 1% (1-ethyl-3-(3-dimethylaminopropyl)carbodiimide hydrochloride) 375 mM (EDC stock) is added and the gold nanorods resuspended 602, then incubated at room temperature for 15 minutes.

The gold nanorods are then spun down again, then a solution of biological probe molecules, in a particular embodiment PNA biopolymer molecules, and an activation buffer containing a mixture of MES buffer and sodium bicarbonate solution with pH7 is added 606. This is sonicated 608 in ice cold water until resuspended and incubated for 2 hours at room temperature while being stirred to form a conjugated nanorod suspension.

Successful conjugation is verified 610 by confirming a spectral shift between the conjugated nanorod suspension and an initial spectrum of the gold nanorods.

Figure 7:
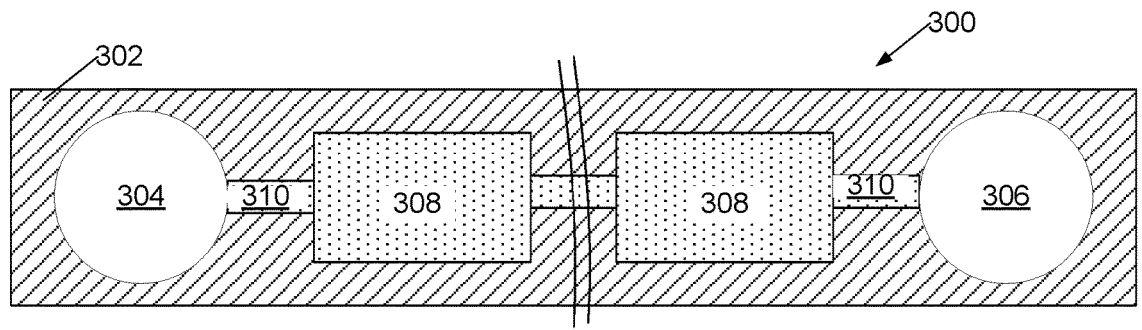
FIG. 7 is a bottom plan view of a microfluidic stamp for forming microfluidic chambers.
Figure 8:
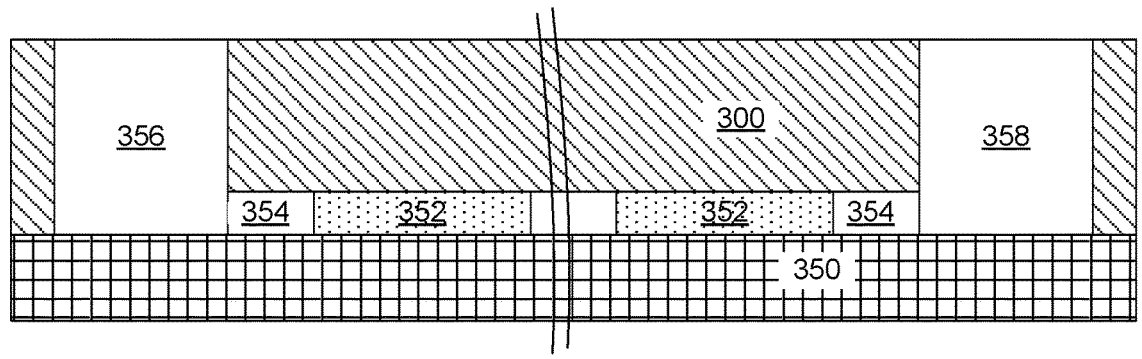
FIG. 8 is a cross sectional view of portions of a chain of microfluidic chambers formed by the stamp of FIG. 6 pressed against stretched and nanowrinkled polymer.
Figure 11:
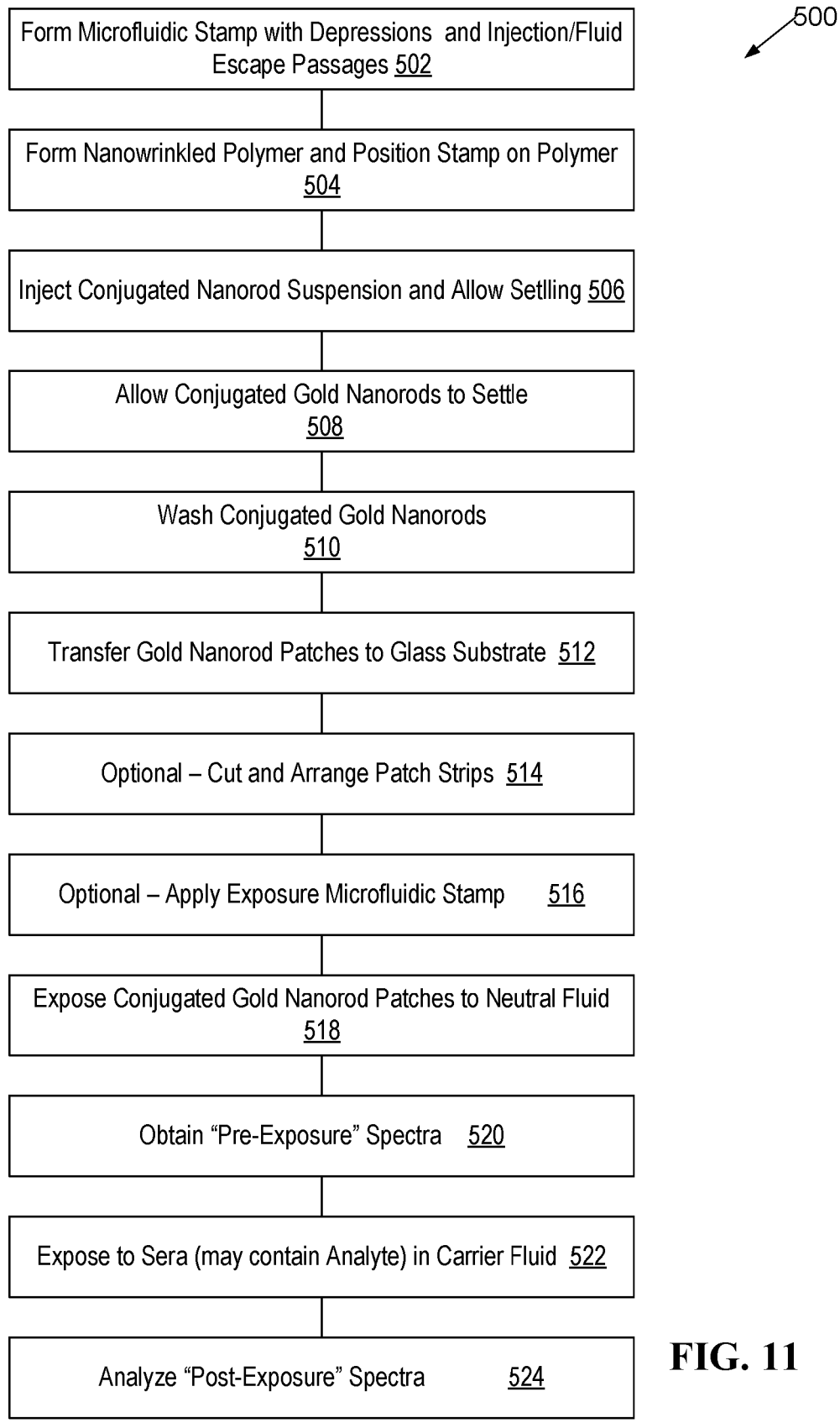
FIG. 11 is a flowchart of a method for making the sensor chip of FIG. 10.

In an embodiment, fabrication 500 of the sensor array begins by forming 502 (FIG. 11) a microfluidic stamp 300 (FIG. 7) having a body 302 sequence of depressions 308 that, when stamp 300 is positioned against stretched, nanowrinkled, polymer 350 (FIG. 8), form microfluidic chambers 352. In an embodiment, nanowrinkled polymer is formed of polydimethylsiloxane (PDMS) cast over a removable photoresist pattern defining depressions 308 Chambers 352 are interconnected by passages 354 formed by narrow depressions 310 in stamp 300 positioned against nanowrinkled polymer 350 forming a chain of chambers 352. At ends of each string of chambers 352 are injection openings 356 formed by an injection passage 304 in stamp 300, and a fluid escape opening 358 formed by a similar passage 306 in stamp 300.

In embodiments, chambers 352 have dimensions in X axis perpendicular to an axis of the chain of chambers of between 100 and 500 micrometers and dimensions in Y axis aligned with of the chain of chambers of between 100 and 500 micrometers. In a particular embodiment, the chambers of size 150 by 250 micrometers and having depth in Z axis of fifty micrometers. The chambers having these dimensions have capacity of 0.025 microliter or less.

Also for definition, a nanorod as used herein has an aspect ratio 1.5 or greater, and a maximum dimension under 500 nanometers (one half micron).

Nanowrinkled polymer 350 has nanowrinkes of fifty to three hundred, and in a particular embodiment 100, nanometers height aligned parallel to the Y axis. It is formed by stretching a PDMS plastic sheet, in an embodiment formed of PDMS resin with a curing agent mixed in a ratio between 5:1 and 10:1 while exposing the sheet to an oxidizing plasma. In experiments, the PDMS sheets were exposed with High=29.6 W, Medium 10.2 W, or Low=7.2 W plasma power. Adjustment of stretch rates and plasma etch has been found to give controllable nanowrinkle depth of 50-300 nanometers and pitch controllable from 100 nanometers to 1.5 micrometers. In an embodiment, medium to high plasma power applied during stretch to a two millimeter thick PDMS sheet gave nanowrinkles of a desirable 100 nanometers depth and 100 nanometers pitch.

Once the chambers are formed by pressing the stamp into nanowrinkled polymer 350, a conjugated gold nanorod suspension is injected 506 at between ten and 100 microliters per minute, and in a particular embodiment fifty microliters per minute into the injection passage 304, the suspension then flows through the chain of chambers 352. The gold nanorods used have aspect ratios of between 1.5 and 5.0, and in a particular embodiment, the conjugated gold nanorods have rectangular cross section with length approximately 124 nanometers and width approximately 40 nanometers. Injection of the fluid is stopped and the nanorods are allowed to settle 508 onto the nanowrinkled polymer 350 under gravity for five minutes.

The microfluidic chambers are then washed 510 with 100 μL of deionized water at a flow rate of 100 microliters per minute to remove excess gold nanorods.

Once settling is complete, and the excess nanorods flushed, in some but not all particular embodiments air may be injected to dry the nanoparticles. It has been found that the nanorods not only settle into rows aligned along the nanowrinkles, but orient themselves with the long dimension of the conjugated nanorods aligned along the nanowrinkles, forming lines of conjugated nanorods, where each conjugated nanorod is aligned along the nanowrinkles. It has also been found that the nanowrinkles must have dimensions approximately of the same order of magnitude as dimensions of the nanoparticles; in an embodiment the nanowrinkles are of width approximately between two and five times the width of the conjugated nanorods. For example, in an experiment with nanoparticles of diameter 100 nanometers it was found that nanowrinkles of size outside the same order of magnitude, being smaller the ten nanometers or larger than one micrometer in width, failed to align the nanoparticles.

Figure 9:
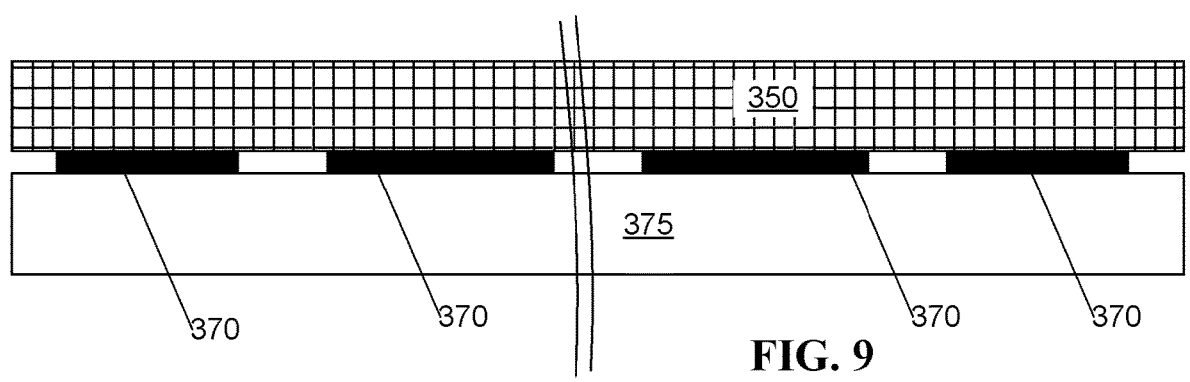
FIG. 9 illustrates transfer of patches of conjugated nanorods from nanowrinkled polymer to a glass substrate.

Stamp 300 is then be removed and the nanowrinkled polymer 350 having patches 370 of oriented conjugated nanorods deposited on it is pressed onto a prepared solid glass substrate 375 as shown in FIG. 9 to transfer 512 the patches 370 of oriented conjugated gold nanorods to a glass substrate. For glass slide transfer, between 30 and 50, and in a particular embodiment 30 microliters (μL) of water was dropped onto the slide, and the wrinkled substrate with rods was placed on top. The nanowrinkled polymer 350 was pressed for a few seconds and the nanowrinkled polymer 350 was removed. In an embodiment, the nanowrinkled polymer 350 and stamp 300 are then cleaned ultrasonically in distilled water for reuse.

Figure 10:
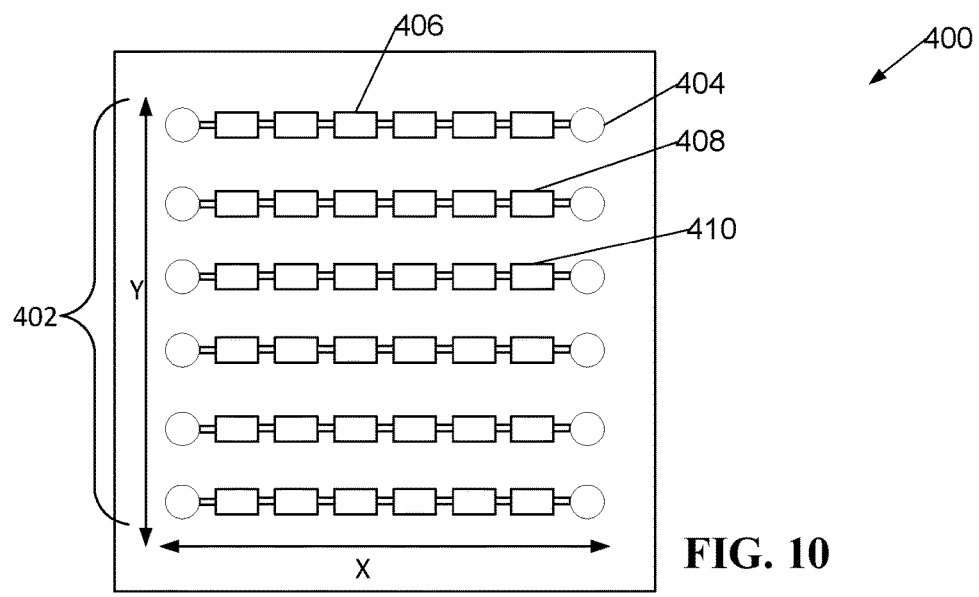
FIG. 10 illustrates multiple chains of patches of conjugated nanorods on a sensor chip.

Stamp 300 may in an embodiment have multiple chains 402 (FIG. 10) of depressions 308, each chain injected through injection ports 404 with gold nanorods conjugated for a different analyte such as a chain 406 conjugated for a first analyte, a chain 408 conjugated for a second analyte, and a control chain conjugated with peptide and absent DNA complementary to an analyte, to form a multi-analyte sensor chip 400. Since chambers of width 150 nanometers can be spaced as little as 100 nanometers apart in the X dimension, a one centimeter sensor chip can have forty chains each conjugated for a different analyte.

The patterned glass substrates substrate may in some embodiments be cut apart 514 parallel to the Y axis to form sensor-patch strips with each patch sensitive to a different analyte, the sensor strips from differently sensitized substrates then assembled parallel to each other forming sensor arrays having 40×N sensor spots, where N is a number of conjugated gold nanorod sensor spots in each chain 402. Since 250-nanometer chambers lead to gold nanorod sensor spots of 250 nanometer width, and these could be spaced 100 nanometers apart, N may be 30 for a one-centimeter sensor array having 1200 sensor spots each sensitized to a different analyte.

In embodiments where the substrates are not cut apart 514, a microfluidic stamp may be applied 516 perpendicular to 514 chains 406, 408, 410 such that the different samples, such as samples from each of several patients, can be applied to individual columns of conjugated gold nanorod patches.

Using the Sensor Array

Once the sensor array is prepared the patches of conjugated bold nanorods are exposed 518 first to a neutral solution not bearing analyte, and spectra from each patch are obtained 520 and stored in memory of a sensor-array reading system. The patches of conjugated gold nanorods are then exposed 522 to sera that may or may not contain analyte(s). Post-exposure spectra from each patch are then obtained 524 and analyzed, in conjunction with the pre-exposure spectra, to quantify each analyte.

Figure 12:
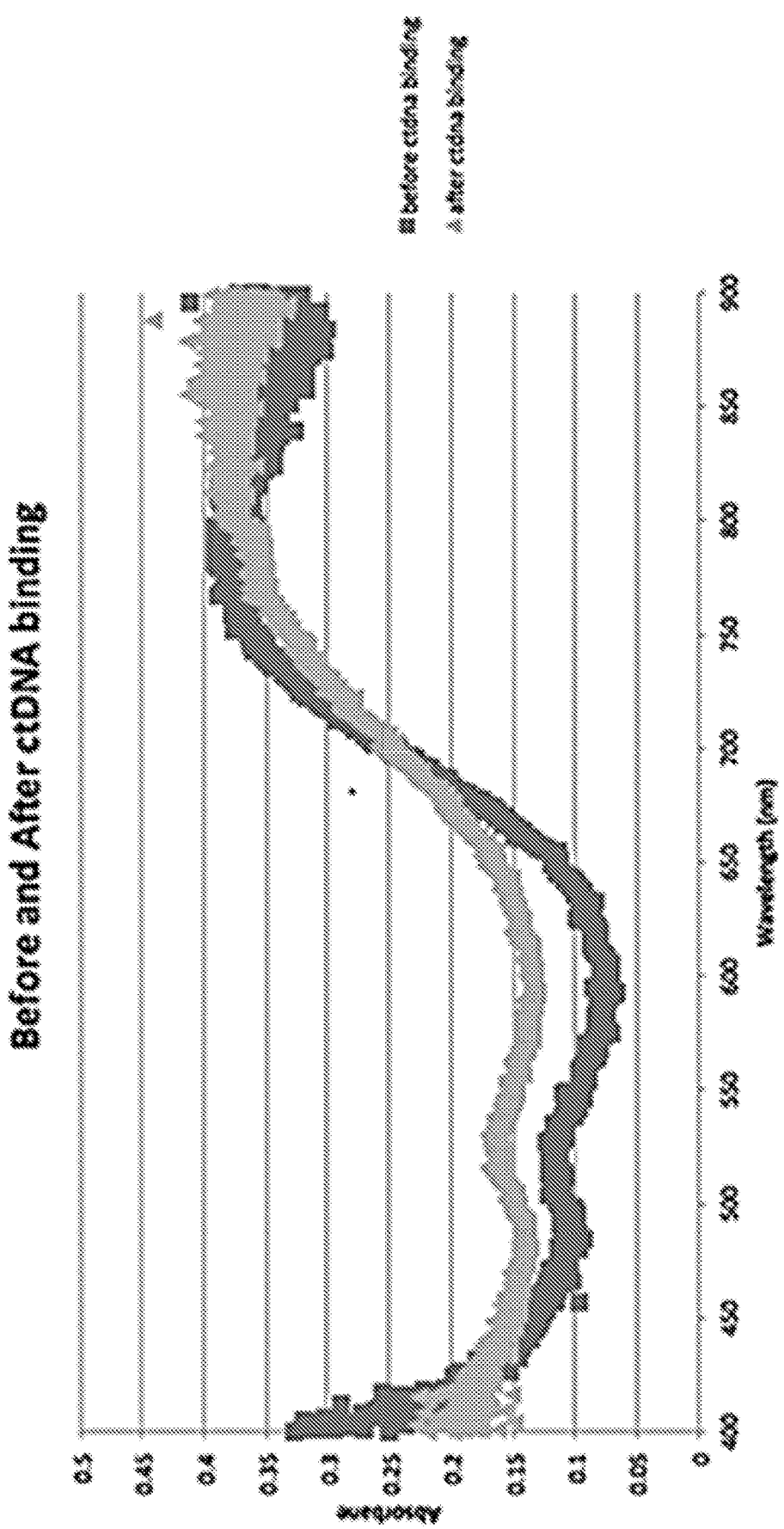
FIG. 12 illustrates shift of spectra when nanorods conjugated to a PNA specific for analyte bind to the analyte, the analyte being a tumor DNA sequence.
Figure 13:
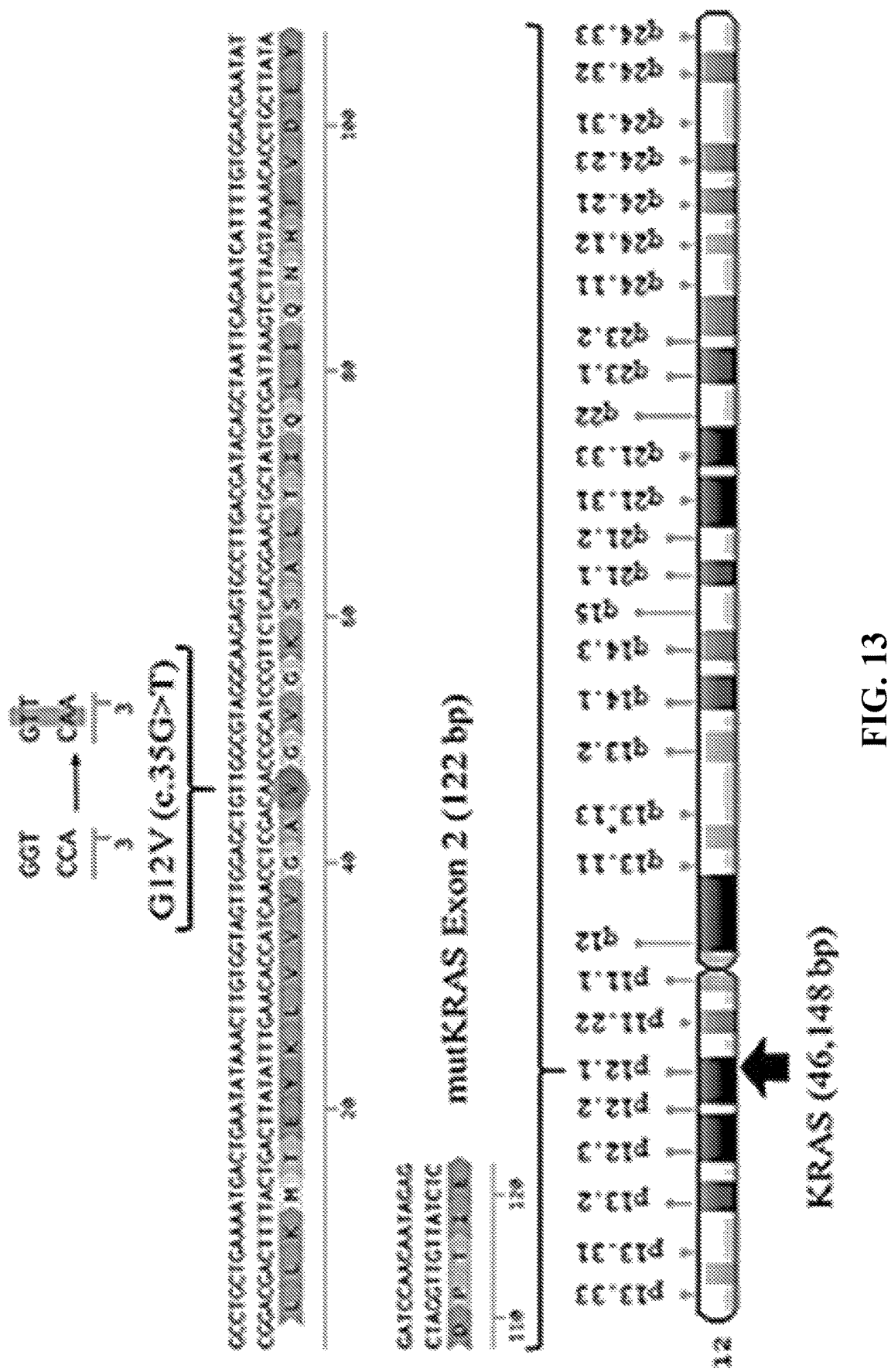
FIG. 13 illustrates a KRAS exon-2 DNA sequence of an analyte.

In a particular experimental embodiment, a PNA was synthesized configured to bear nucleotides complementary to a DNA sequence, the KRAS-2 exon (FIG. 13), found in circulatory blood sera in patients with some pancreatic tumors. When this PNA was bound to nanorods and sensors prepared according to the procedure described herein, a significant spectral shift as illustrated in FIG. 12 was found to occur when DNA of this sequence binds to the nanorods.

In an alternative embodiment, the sensor array is operated as a concentrator. In this embodiment, once the sensor array is fabricated, a large volume of sera potentially containing analyte is passed through microfluidic chambers each having at least one patch having gold nanorods conjugated with selective biological probe materials that bind to that analyte. After the sera potentially containing analyte has run through the chambers, an eluting solution is passed over the conjugated gold nanorods; the eluting solution has characteristics, such as a different pH or high-binding-coefficient analyte analogs, which cause the conjugated gold nanorods to release any analyte they have bound into the eluting solution. Since the eluting solution can be a smaller volume solution than the sera, eluting solution drained from the microfluidic chambers may have analyte at far higher concentration than in the sera.

Combinations of Features

The features and steps herein described may be implemented in various sequences and combinations. Among combinations anticipated are:

A method designated A of making a plasmon-resonance biosensor including conjugating precious metal nanorods, the nanorods having a long dimension greater than a narrow dimension by a factor of at least 1.5 and the long dimension less than one half micron, with a biological probe material capable of binding to an analyte; forming a plurality of microfluidic chambers, each chamber having volume less than 0.025 microliter, over a substrate; and injecting an aqueous suspension of the conjugated precious metal nanorods into the microfluidic chambers. The method continues with organizing the conjugated precious metal nanorods in rows of conjugated precious metal nanorods; and aligning a long dimension of the conjugated precious metal nanorods along the rows of conjugated precious metal nanorods; to produce a sensor wherein the plasmon-resonance biosensor is configured to be read by obtaining an optical absorption spectrum upon exposure to the analyte.

A method designated AA including the method designated A where the step of forming a plurality of microfluidic chambers is performed by mating a stamp to a nanowrinkled substrate, the nanowrinkled substrate having nanowrinkles with depth less than 300 nanometers, and pitch less than 500 nanometers; and the organizing the conjugated precious metal nanorods in rows and aligning the long dimension of the conjugated precious metal nanorods along the rows is performed by gravitational settling of the conjugated precious metal nanorods into the nanowrinkles.

A method designated AB including the method designated A or AA wherein the nanowrinkles are aligned with a direction of flow in the microfluidic chambers of the aqueous suspension of the conjugated nanoparticles.

A method designated AC including the method designated A, AA, or AB and further including removing the stamp and transferring the rows of conjugated precious metal nanorods from the nanowrinkled substrate onto a glass substrate.

A method designated AD including the method designated A, AA, AB or AC wherein the biological probe material comprises a protein-nucleic acid (PNA) compound.

A method designated AE including the method designated A, AA, AB or AC wherein the biological probe material comprises an antibody.

A method designated AF including the method designated A, AA, AB or AC wherein the biological probe material comprises a strand of DNA complimentary to an analyte DNA.

A method designated AG including the method designated A, AA, AB or AC wherein the biological probe material comprises an aptamer.

A method designated AH including the method designated A, AA, AB or AC wherein the biological probe material comprises a protein having a binding site for an analyte.

A method designated AJ including the method designated A, AA, AB, AC, AE, AF, AG, or AH wherein the biological probe material is configured to bind to deoxyribose nucleic acid (DNA) strands released by a particular tumor type.

A method designated AK including the method designated AJ wherein the particular tumor type is a pancreatic cancer.

A method designated AL including the method designated A, AA, AB, AC, AE, AF, AG, or AH wherein the precious metal nanorods comprise gold nanorods.

A plasmon-resonance biosensor designated B including a plurality of precious metal nanorods, the precious metal nanorods having a long dimension greater than a narrow dimension by a factor of at least 1.5 and a maximum dimension less than one half micron; the nanorods organized in rows; the nanorods in the rows are oriented with the long dimension approximately parallel to the rows; the precious metal nanorods conjugated with a biological probe material capable of binding to an analyte, the biological probe material being selected from the group consisting of an aptamer, an antibody, a protein-nucleic acid (PNA), a complimentary DNA, and an enzyme having a binding site.

A plasmon-resonance biosensor designated BA including the plasmon resonance biosensor designated B wherein the precious metal nanorods include gold.

A plasmon-resonance biosensor designated BB including the plasmon resonance biosensor designated B or BA wherein the biological probe material is a PNA configured to bind to a tumor-specific DNA.

A plasmon-resonance biosensor designated BC including the plasmon resonance biosensor designated B, BA, or BB wherein the precious metal nanorods are disposed in a plurality of patches on a substrate, with at least a first patch conjugated with a first biological probe material and a second patch on the same substrate conjugated with a second biological probe material A test system designated C and including the plasmon-resonance biosensor designated B, BA, BB, or BC, and an optical absorption spectrometer configured to scan the plurality of patches of precious metal nanorods.

CONCLUSION

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A plasmon-resonance biosensor comprising:
   a plurality of precious metal nanorods, the precious metal nanorods having a long dimension greater than a narrow dimension by a factor of at least 1.5 and a maximum dimension less than one half micron;
   the nanorods organized in rows;
   the nanorods in the rows are oriented with the long dimension approximately parallel to the rows;
   the precious metal nanorods are conjugated with a biological probe material capable of binding to an analyte, the biological probe material, is a protein-nucleic acid (PNA) or a complimentary DNA.

2. The plasmon-resonance biosensor of claim 1 wherein the precious metal nanorods comprise gold.

3. The plasmon-resonance biosensor of claim 2 wherein the biological probe material is a PNA configured to bind to a tumor-specific DNA.

4. The plasmon-resonance biosensor of claim 1 wherein the precious metal nanorods are disposed in a plurality of patches on a substrate, with at least a first patch conjugated with a first biological probe material and a second patch on the same substrate conjugated with a second biological probe material.

5. A test system comprising the plasmon-resonance biosensor of claim 4 and an optical absorption spectrometer configured to scan the plurality of patches of precious metal nanorods.

6. The plasmon-resonance biosensor of claim 4 further comprising a sensor-array reading system configured to expose the plasmon resonance biosensor first to a neutral solution not bearing analyte, and record pre-exposure spectra from each patch, to then expose the plasmon resonance biosensor to sera that may or may not contain analyte and obtain post-exposure spectra from each patch, and to compare the post-exposure spectra from each patch to the pre-exposure spectra from each patch.

7. The plasmon-resonance biosensor of claim 1 where the biological probe material is PNA.

8. The plasmon-resonance biosensor of claim 1 formed on a glass substrate.

9. A method of making a plasmon-resonance biosensor comprising:
   conjugating precious metal nanorods, the nanorods having a long dimension greater than a narrow dimension by a factor of at least 1.5 and the long dimension less than one half micron, with a biological probe material capable of binding to an analyte;
   forming a plurality of microfluidic chambers, each chamber having volume less than 0.025 microliter, over a substrate;

injecting an aqueous suspension of the conjugated precious metal nanorods into the microfluidic chambers;

organizing the conjugated precious metal nanorods in rows of conjugated precious metal nanorods; and aligning a long dimension of the conjugated precious metal nanorods along the rows of conjugated precious metal nanorods;

wherein the plasmon-resonance biosensor is configured to be read by obtaining an optical absorption spectrum upon exposure to the analyte.

10. The method of claim 9 wherein:

the step of forming a plurality of microfluidic chambers is performed by mating a stamp to a nanowrinkled substrate, the nanowrinkled substrate having nanowrinkles with depth less than 300 nanometers, and pitch less than 500 nanometers;

the organizing the conjugated precious metal nanorods in rows and aligning the long dimension of the conjugated precious metal nanorods along the rows is performed by gravitational settling of the conjugated precious metal nanorods into the nanowrinkles.

11. The method of claim 10 wherein the nanowrinkles are aligned with a direction of flow in the microfluidic chambers of the aqueous suspension of the conjugated nanoparticles.

12. The method of claim 10 further comprising:

removing the stamp and transferring the rows of conjugated precious metal nanorods from the nanowrinkled substrate onto a glass substrate.

13. The method of claim 9, wherein the biological probe material comprises a protein-nucleic acid (PNA) compound.

14. The method of claim 13 wherein the PNA is configured to bind to deoxyribose nucleic acid (DNA) strands released by a particular tumor type.

15. The method of claim 14 wherein the particular tumor type is a pancreatic cancer.

16. The method of claim 13 wherein the precious metal nanorods comprise gold nanorods.

17. The method of claim 9, wherein the biological probe material comprises a strand of DNA complimentary to an analyte DNA.

18. The method of claim 17 wherein the biological probe material is configured to bind to deoxyribose nucleic acid (DNA) strands released by a particular tumor type.

19. The method of claim 18 wherein the particular tumor type is a pancreatic cancer.

* * * * *